(12) United States Patent
Wang et al.

(10) Patent No.: US 10,151,018 B2
(45) Date of Patent: Dec. 11, 2018

(54) SELECTIVE EXTRACTION OF SEDIMENTOGENIC STRONTIUM AND BARIUM IN TERRIGENOUS CLASTIC SEDIMENTS

(71) Applicant: Nanjing Center of Geological Survey, China Geological Survey, Nanjing (CN)

(72) Inventors: Aihua Wang, Nanjing (CN); Jiankun Liu, Nanjing (CN); Fei Zhang, Nanjing (CN); Hualing Li, Nanjing (CN)

(73) Assignee: Nanjing Center of Geological Survey, China Geological Survey, Nanjing (CN)

( * ) Notice: Subject to any disclaimer, the term of this patent is extended or adjusted under 35 U.S.C. 154(b) by 0 days.

(21) Appl. No.: 15/600,406

(22) Filed: May 19, 2017

(65) Prior Publication Data
US 2018/0187288 A1 Jul. 5, 2018

(30) Foreign Application Priority Data
Dec. 30, 2016 (CN) .......................... 2016 1 1260917

(51) Int. Cl.
| | |
|---|---|
| *C22B 3/16* | (2006.01) |
| *C22B 26/10* | (2006.01) |
| *G01N 1/40* | (2006.01) |
| *G01N 1/44* | (2006.01) |
| *G01N 33/24* | (2006.01) |
| *G01N 1/28* | (2006.01) |

(52) U.S. Cl.
CPC ................ *C22B 26/10* (2013.01); *C22B 3/16* (2013.01); *G01N 1/4044* (2013.01); *G01N 1/44* (2013.01); *G01N 33/24* (2013.01); *G01N 2001/2866* (2013.01)

(58) Field of Classification Search
CPC ...................................................... C22B 26/10
See application file for complete search history.

(56) References Cited

U.S. PATENT DOCUMENTS 3,154,500 A * 10/1964 Jansen, Jr. ............ C22B 3/0095
252/644

* cited by examiner

*Primary Examiner* — Melissa S Swain
(74) *Attorney, Agent, or Firm* — Timothy T. Wang; Ni, Wang & Massand, PLLC

(57) ABSTRACT

A method for selectively extracting sedimentogenic strontium and barium from terrigenous elastic sediments to reflect the difference between marine and continental sedimentary environments is disclosed. The method comprises collecting loose sediment, removing visible biogenic clasts, baking the sample and crushing the sample to a grain size no larger than 100-mesh. The method further comprises weighing the sample, reacting the sample in acetic acid or acetic acid-acetate solution, stirring or oscillating the sample at room temperature and normal pressure, separating the solid and liquid after reaction and analyzing strontium and barium in the supernatant. The gained Sr/Ba ratio of the supernatant reflects whether the sediments were deposited in a marine or a continental sedimentary environment.

14 Claims, 1 Drawing Sheet

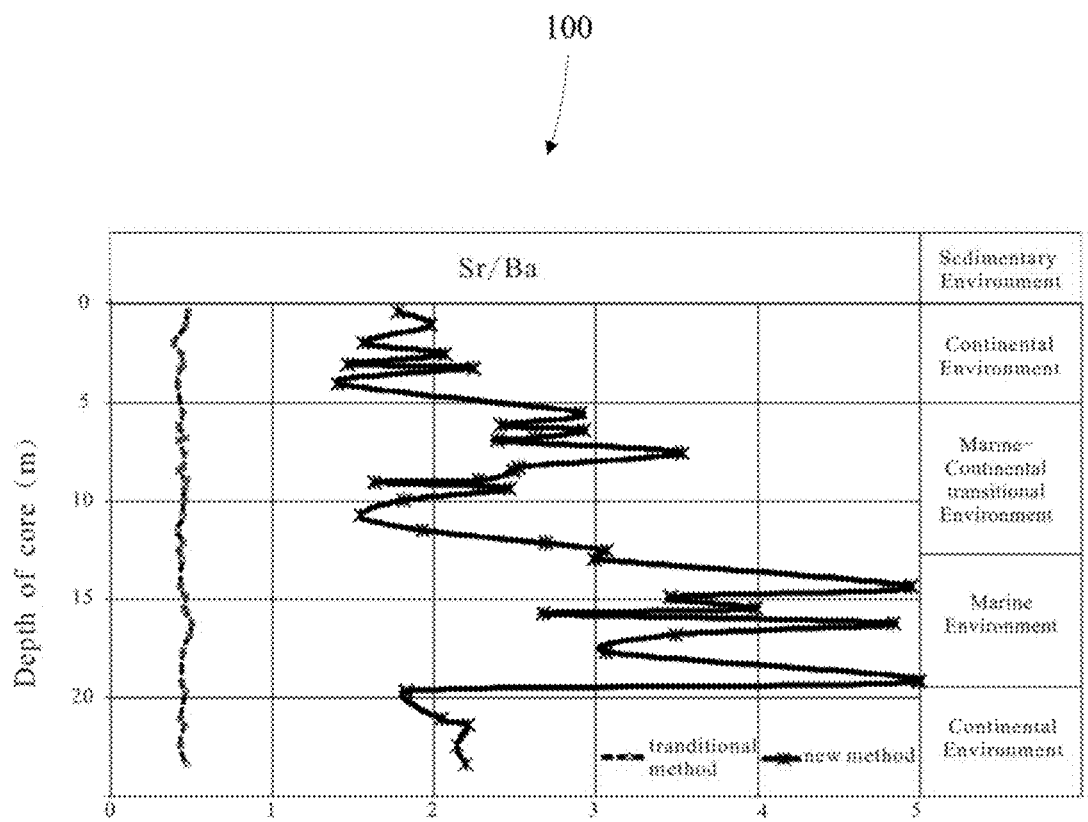

SELECTIVE EXTRACTION OF SEDIMENTOGENIC STRONTIUM AND BARIUM IN TERRIGENOUS CLASTIC SEDIMENTS

BACKGROUND

The present disclosure is generally related to selective extraction of Strontium (Sr) and Barium (Ba) from sediment to determine marine or continental sedimentary environments of terrigenous elastic sediments.

Strontium (Sr) and Barium (Ba) are alkaline earth metals and exhibit similar geochemical behaviors in endogenous geological processes. However, due to differences in their chemical properties, they behave differently in exogenetic sedimentary processes. Because the differences in the geochemical environments between rivers and the sea (e.g., Eh, pH, salinity, and the concentrations of other ions), especially in estuaries where seawater and river water interact, due to the different geochemical behaviors of Sr and Ba in the ionic state in water, the result is that continental terrigenous elastic sediments are enriched in Ba, whereas marine terrigenous elastic sediments are enriched in Sr. Therefore, the Sr/Ba ratio may be used to distinguish marine or continental sedimentary environments of terrigenous elastic sediments.

At present, many sedimentary scientists and sedimentary geochemists use the Sr/Ba ratio obtained by whole-rock chemical analysis or bulk sample analysis of terrigenous elastic sediments to discriminate between marine and continental sedimentary environment, but the discrimination results may be unsatisfactory. The main reason is that the sample pretreatment methods used by most of the researchers in the analysis are inappropriate. Because the concentration of Sr and Ba measured by whole-rock analysis consists of two parts: a part is from the elastic minerals reflecting geological background information of the material source regions (structure environment rock type, weathering characteristics), and another part comes into being during sedimentary processes reflecting marine or continental sedimentary geochemical environment changes (sedimentogenic Sr and Ba).

Currently, sedimentologists and sedimentary geochemists primarily use two types of analytical methods to measure Sr and Ba in elastic sediments. The first analytical method is X-ray fluorescence spectroscopy (XRF methods, including the pressed powder pellet method and fused glass bead method), the other method is inductively coupled plasma optical emission spectrometry or inductively coupled plasma mass spectrometry (ICP-OES or ICP-MS, abbreviated as ICP methods). The XRF methods involve crushing a bulk sample to 200-mesh, pressing powder or fused glass, then measuring a bulk sample element content. The ICP methods involve crushing a bulk sample to 200-mesh, digesting all the elements in a solution, then measuring the concentrations of elements with an appropriate ICP instrument. The current most commonly used ICP methods for digesting geological samples are acid digestion (via hydrochloric acid, nitric acid, hydrofluoric acid, and perchloric acid) and fusion (lithium tetraborate or lithium metaborate fusion followed by dilute acid extraction). However, both are whole-rock chemical analysis. Using the above analytical methods, the analytical results of modern sediments represent the total amounts of Sr and Ba in the bulk samples. However, to distinguish sedimentary environments, what we need is the sedimentogenic Sr and Ba contents in elastic sediments, not the total Sr and Ba contents should be determined. A new sample pretreatment method may selectively extract the sedimentogenic Sr and Ba from terrigenous elastic sediments in order to use the Sr/Ba ratio to distinguish between marine and continental sedimentary environments.

SUMMARY

In one embodiment, a method of selective extracting strontium and barium from sediments, comprises at least one of, a suitable amount of representative loose sediment is collected, visible biogenic clasts (shells, etc.) are removed, and the sample is baked at a low temperature and then crushed to a grain size no larger than 100-mesh, reacting a portion of the sample in a solution containing acetic acid or acetic acid-acetate, measuring strontium within a liquid product of the solution, measuring barium within the liquid product of the solution and calculating a ratio of the strontium and barium of the sediments.

In another embodiment, a method of selective extracting strontium and barium from sediments, comprises at least one of, a suitable amount of representative loose sediment is collected, visible biogenic clasts (shells, etc.) are removed, and the sample is baked at a low temperature and then crushed to a grain size no larger than 100-mesh (about 150 microns) in size, stirring or oscillating the sample in an acetic acid solution or acetic acid-acetate buffer solution, measuring strontium within a liquid product, measuring barium within the liquid product and gaining a ratio of the strontium and barium of the sediments.

BRIEF DESCRIPTION OF THE DRAWINGS

FIG. 1 depicts a comparison of Sr/Ba in marine and continental sediment in accordance with one embodiment of the disclosure and according to current techniques.

DETAILED DESCRIPTION

It may be readily understood that the components of the present application, as generally described and illustrated in the figures herein, may be arranged and designed in a wide variety of different configurations. Thus, the following detailed description of the examples of a method as represented in the attached figures, is not intended to limit the scope of the application as claimed, but is merely representative of selected examples of the application.

The features, structures, or characteristics of the application described throughout this specification may be combined in a suitable manner in one or more examples. For example, the usage of the phrases example, examples, some examples, or other similar language, throughout this specification refers to the fact that a particular feature, structure, or characteristic described in connection with the example may be comprised in at least one example of the present application. Thus, appearances of the phrases example, examples, in some examples, in other examples, or other similar language, throughout this specification does not necessarily refer to the same group of examples, and the described features, structures, or characteristics may be combined in a suitable manner in one or more examples.

The objective of this new technique is to selectively extract the sedimentogenic Sr and Ba from the total Sr and Ba in multiple forms derived from multiple sources, thereby eliminating the interference of non-sedimentogenic Sr and Ba, which may constitute more than 50% of the total amount. Thus, this selective extraction may allow the Sr/Ba ratio to distinguish between marine and continental sedimentary environments.

The Sr and Ba in terrigenous elastic sediments may exist in many forms. They may occur in rock-forming minerals (including K-feldspar, plagioclase, and amphibole and so on), in adsorbed forms or as ions in clay minerals formed by weathering, transport, and deposition processes, and in authigenic minerals formed in sedimentary processes. The Sr and Ba may be exchangeable and carbonates bound, Fe—Mn oxides bound, organic and reduction materials bound, and residual (vast majority is silicate minerals) in terrigenous elastic sediments. However, regardless of origin, source, and form of existence, what we need is to try to extract only the sedimentogenic Sr and Ba from terrigenous elastic sediments for distinguishing between marine and continental sedimentary environments, but because of the complexity of the genesis and occurrence of elements in sediments, it has been difficult to achieve reliably. But it can be done that as far as possible to reduce the interference of non-sedimentogenic Sr and Ba unrelated to sedimentary environments, the selective extraction method of the present disclosure provides one such reliable method.

One technical issue that this method may solve is finding a reliable extraction agent and method for extracting the sedimentogenic Sr and Ba, which reflect the characteristics of the sedimentary environment, from the multi-genesis, multi-source, and multi-occurrence form Sr and Ba in terrigenous elastic sediments.

Previous studies have found that approximately 50% of the Sr in terrigenous elastic sediments is present in silicate rock-forming minerals (including K-feldspar, plagioclase, and amphibole and so on), and that approximately 40% is in exchangeable forms and bound to carbonates. More than 80% of the Ba is present in silicate rock-forming minerals (including K-feldspar, plagioclase, and amphibole and the like), and less than 10% is in exchangeable forms and bound to carbonates or Fe—Mn oxides. Silicate rock-forming minerals, including K-feldspar, plagioclase, and amphibole and so on, are generally riot digested by acids other than hydrofluoric acid. This property allows the selective extraction of sedimentogenic Sr and Ba from elastic sediments and eliminating interfere of non-sedimentogenic Sr and Ba related to the provenance.

To use the Sr/Ba, ratio to discriminate between marine and continental sedimentary environment, multiple common acids, complexing agents, and their combinations were tested to obtain a reliable selective extraction agent and method.

A suitable amount of representative terrigenous elastic sediments are collected, visible biogenic clasts (shells, etc.) are eliminated, the sample is baked at low a temperature, then crushed to a grain size no larger than 100-mesh. The sample is weighed and acetic acid solution or acetic acid-acetate buffer solution is added with a 5-50% acetic acid mass concentration as an extraction agent in 1:50-1:500 solid-liquid ratio. The sample and acid are stirred or oscillated (ultrasonic oscillation is also an option) at room temperature (20-30° C.) and normal pressure for more than 60 minutes. The solid and liquid are separated, and the supernatant is diluted to an appropriate concentration for the instrumental analysis (by ICP-OES or ICP-MS) of Sr and Ba. The gained Sr/Ba ratio reflects whether the sediment was deposited in a marine or a continental sedimentary environment.

Compared to conventional whole-rock chemical analysis methods, the present method uses a more reliable extraction agent and method that extracts predominately sedimentogenic Sr and Ba from terrigenous elastic sediments in order to better distinguish between marine and continental sedimentary environments. This method avoids the interference of non-sedimentogenic Sr (which can represent more than 50% of the total amount) and non-sedimentogenic Ba (which can represent more than 80% of the total amount) in elastic sediments. It thereby increases the resolution, effectiveness, and accuracy of using the Sr/Ba ratio to distinguish between marine and continental sedimentary environments and may solve a basic theoretical problem that has troubled the fields of sedimentology and sedimentary geochemistry. Particularly, this analytical measurement method is simple, fast and reliable.

Based on the disclosed method, the following examples are presented to illustrate and explain this invention, but not to limit its range of applications.

EXAMPLE 1

The selective extraction method for sedimentogenic Sr and Ba in terrigenous elastic sediments includes the following steps. A suitable amount of representative loose sediment is collected, and visible biogenic clasts (shells, etc.) are removed. The sample is baked at a low temperature and crushed to a grain size no larger than 100-mesh. A suitable amount of the sample is weighed, and an acetic acid solution or acetic acid-acetate buffer solution with a 50% mass concentration of acetic acid added as an extraction agent at a 1:50 solid-liquid ratio. The mixture is stirred or oscillated (ultrasonic oscillation is also an option) at room temperature (20-30° C.) and normal pressure for more than 60 minutes, and the solid and liquid are separated. The supernatant is diluted to an appropriate concentration for the instrumental analysis (by ICP-OES or ICP-MS) of the Sr and Ba concentrations. The gained Sr/Ba ratio reflects whether the sample was deposited in a marine or continental sedimentary environment.

EXAMPLE 2

The selective extraction method for sedimentogenic Sr and Ba in terrigenous elastic sediments includes the following steps. A suitable amount of representative loose sediment is collected, and visible biogenic clasts (shells, etc.) are removed. The sample is baked at a low temperature and crushed to a grain size no larger than 100-mesh. A suitable amount of the sample is weighed, and an acetic acid solution or acetic acid-acetate buffer solution with a 40% mass concentration of acetic acid is added as an extraction agent at a 1:100 solid-liquid ratio. The mixture is stirred or oscillated (ultrasonic oscillation is also an option) at room temperature (20-30° C.) and pressure for more than 60 minutes, and the solid and liquid are separated. The supernatant is diluted to an appropriate concentration for the instrumental analysis (by ICP-OES or ICP-MS) of the Sr and Ba concentrations. The gained Sr/Ba ratio reflects whether the sample was deposited in a marine or continental sedimentary environment.

EXAMPLE 3

The selective extraction method for sedimentogenic Sr and Ba in terrigenous elastic sediments includes the following steps. A suitable amount of representative loose sediment is collected, and visible biogenic clasts (shells, etc.) are removed. The sample is baked at a low temperature and crushed to a grain size no larger than 100-mesh. A suitable amount of the sample is weighed, and an acetic acid solution or acetic acid-acetate buffer solution with a 30% mass concentration of acetic acid is added as an extraction agent at a 1:200 solid-liquid ratio, The mixture is stirred or oscillated (ultrasonic oscillation is also an option) at room temperature (20-30° C.) and pressure for more than 60 minutes, and the solid and liquid are separated. The supernatant is diluted to an appropriate concentration for the instrumental analysis (by ICP-OES or ICP-MS) of the Sr and Ba concentrations. The gained Sr/Ba ratio reflects whether the sample was deposited in a marine or continental sedimentary environment.

EXAMPLE 4

The selective extraction method for sedimentogenic Sr and Ba in terrigenous elastic sediments includes the following steps. A suitable amount of representative loose sediment is collected, and visible biogenic clasts (shells, etc.) are removed. The sample is baked at a low temperature and crushed to a grain size no larger than 100-mesh. A suitable amount of the sample is weighed, and an acetic acid solution or acetic acid-acetate buffer solution with a 20% mass concentration of acetic acid is added as an extraction agent at a 1:400 solid-liquid ratio. The mixture is stirred or oscillated (ultrasonic oscillation is also an option) at room temperature (20-30° C.) and pressure for more than 60 minutes, and the solid and liquid are separated. The supernatant is diluted to an appropriate, concentration for the instrumental analysis (by ICP-OES or ICP-MS) of the Sr and Ba concentrations. The gained Sr/Ba ratio reflects whether the sample was deposited in a marine or continental sedimentary environment.

EXAMPLE 5

The selective extraction method for sedimentogenic Sr and Ba in terrigenous elastic sediments includes the following steps. A suitable amount of representative loose sediment is collected, and visible biogenic clasts (shells, etc.) are removed. The sample is baked at a low temperature and crushed to a grain size no larger than 100-mesh. A suitable amount of the sample is weighed, and an acetic acid solution or acetic acid-acetate buffer solution with a 5% mass concentration of acetic acid is added as an extraction agent at a 1:500 solid-liquid ratio. The mixture is stirred or oscillated (ultrasonic oscillation is also an option) at room temperature (20-30° C.) and pressure for more than 60 minutes, and the solid and liquid are separated. The supernatant is diluted to an appropriate concentration for the instrumental analysis (by ICP-OES or ICP-MS) of the Sr and Ba concentrations. The gained Sr/Ba ratio reflects whether the sample was deposited in a marine or continental sedimentary environment.

FIG. 1 shows the results from a ZK5 drill core samples from the Yellow River delta are used as an example using a conventional technique on the left and the technique of the present disclosure on the right. This sample series features are: continental facies at the top of the core, marine-continental transitional facies near the top and middle of the core, marine facies in the middle and bottom of the core, and continental facies at the bottom of the core. Using the conventional method on the left, the highest Sr/Ba ratio is 0.50, the lowest is 0.39, and the variation in the ratio does not clearly show a correlation with the sedimentary environment. Therefore, conventional Sr/Ba ratio does not distinguish between marine and continental sedimentary environments. The technique of the present disclosure is shown on the right and indicates a clear signal differentiating the sedimentary environment of marine facies or marine-continental transitional facies or continental transitional facies.

Although exemplary examples the method of the present disclosure have been illustrated in the accompanied drawings and described in the foregoing detailed description, it will be understood that the application is not limited to the examples disclosed, and is capable of numerous rearrangements, modifications, and substitutions without departing from the spirit or scope of the disclosure as set forth and defined by the following claims.

The above examples are for illustrative purposes and are not intended to limit the scope of the disclosure or the adaptation of the features described herein to particular components. Those skilled in the art will also appreciate that various adaptations and modifications of the above-described preferred examples may be configured without departing from the scope and spirit of the disclosure. Therefore, it is to be understood that, within the scope of the appended claims, the disclosure may be practiced by examples in addition to those specifically described.

What is claimed is:

1. A method of selective extracting strontium and barium from sediments, comprising:
    collecting a sample of loose sediment;
    removing visible biogenic clasts such as shells;
    baking the sample to remove water and volatiles with a temperature less than 105° C.;
    crushing the baked sample to no larger than 100-mesh;
    reacting a portion of the sample in a solution containing acetic acid or acetic acid-acetate;
    measuring strontium within a liquid product of the solution;
    measuring barium within the liquid product of the solution; and
    calculating a ratio of the strontium and barium of the liquid product.

2. The method of claim 1 wherein a ratio of strontium to barium is calculated.

3. The method of claim 1 wherein a ratio of barium to strontium is calculated.

4. The method of claim 1 wherein an acetic acid mass concentration in the acetic acid solution or acetic acid-acetate buffer solution is between 5-50%.

5. The method of claim 1 wherein a solid-liquid ratio of the sample and extraction agent is between 1:50-1:500.

6. The method of claim 1 wherein the sample grain size after crushing must not be greater than 100-mesh (less than 150 microns).

7. The method of claim 1 further comprising stirring or oscillating the solution and at least sixty minutes in duration.

8. The method of claim 7 wherein the oscillating is at least one of mechanical or ultrasonic.

9. The method of claim 1 wherein the baking is at least twelve hours in duration.

10. A method of extracting strontium and barium from sediments, comprising:
    crushing a sedimentary sample;
    reacting a portion of the sedimentary sample in a solution containing acetic acid or acetic acid-acetate;
    measuring strontium within a liquid product;
    measuring barium within the liquid product; and
    calculating a ratio of the strontium and barium of the liquid product.

11. The method of claim 10 wherein a ratio of strontium to barium is determined.

12. The method of claim 10 wherein a ratio of barium to strontium is determined.

13. The method of claim 10 wherein an acetic acid mass concentration in the acetic acid solution is between 5-50%.

14. The method of claim 10 wherein a solid-liquid ratio of the sample and extraction agent is between 1:50-1:500.

* * * * *